US012761197B2

(12) United States Patent
Park et al.

(10) Patent No.: US 12,761,197 B2
(45) Date of Patent: Oct. 13, 2026

(54) LEAKAGE INSPECTING SYSTEM FOR INSPECTION TARGET

(71) Applicants: Hyundai Motor Company, Seoul (KR); Kia Corporation, Seoul (KR)

(72) Inventors: Jae Hyeon Park, Seoul (KR); In Sun Lee, Seoul (KR); Jae Ho Hwang, Seoul (KR); Min Ho Woo, Seoul (KR)

(73) Assignees: Hyundai Motor Company, Seoul (KR); Kia Corporation, Seoul (KR)

(*) Notice: Subject to any disclaimer, the term of this patent is extended or adjusted under 35 U.S.C. 154(b) by 282 days.

(21) Appl. No.: 18/762,338

(22) Filed: Jul. 2, 2024

(65) Prior Publication Data

US 2025/0216368 A1 Jul. 3, 2025

(30) Foreign Application Priority Data

Dec. 29, 2023 (KR) ........................ 10-2023-0197535

(51) Int. Cl.
*G01N 33/00* (2006.01)

(52) U.S. Cl.
CPC ..... *G01N 33/0016* (2013.01); *G01N 33/0036* (2013.01)

(58) Field of Classification Search
None
See application file for complete search history.

(56) References Cited

U.S. PATENT DOCUMENTS 10,473,550 B2 * 11/2019 Li ........................... G01M 3/00

FOREIGN PATENT DOCUMENTS

| | | | | | |
|---|---|---|---|---|---|
| CN | 210319411 U | | 4/2020 | | |
| JP | 4961639 B2 | | 6/2012 | | |
| KR | 20140056922 A | * | 5/2014 | ............ | G01N 27/12 |

* cited by examiner

*Primary Examiner* — Peter J Macchiarolo
*Assistant Examiner* — Jermaine L Jenkins
(74) *Attorney, Agent, or Firm* — Fox Rothschild LLP

(57) ABSTRACT

The present disclosure relates to a leakage inspecting system for an inspection target, and the leakage inspecting system for an inspection target includes a supply part that supplies a leak inspection gas to the inspection target, a suction part that includes a plurality of inspection pipes facing a plurality of inspection points on the inspection target and suctions the leak inspection gas leaked from the plurality of inspection points through the inspection pipes facing the inspection points, a sensing part that is connected to the suction part and measures a suction amount of the leak inspection gas suctioned through the suction part, and a discharge part that discharges a remaining gas in the inspection target or the suction part to the outside.

20 Claims, 4 Drawing Sheets

LEAKAGE INSPECTING SYSTEM FOR INSPECTION TARGET

CROSS-REFERENCE TO RELATED APPLICATION

This application claims under 35 U.S.C. § 119(a) the benefit of Korean Patent Application No. 10-2023-0197535, filed in the Korean Intellectual Property Office on Dec. 29, 2023, the entire contents of which are incorporated herein by reference.

BACKGROUND

Technical Field

The present disclosure relates to a leakage inspecting system for an inspection target.

Background

A fuel cell is a type of power generating device that electrochemically reacts a fuel inside a stack and converts the fuel into electrical energy while chemical energy of the fuel is not converted into heat through combustion. After a plurality of unit cells are laminated, a current collector, an insulating plate, and an end plate for supporting the laminated cells are coupled to the outermost side thereof, and the unit cells are repeatedly laminated and fastened between the end plates to constitute a fuel cell stack.

Meanwhile, a fuel processing system (FPS) is a system that adjusts a pressure of hydrogen supplied from a hydrogen tank that is a fuel tank and supplies the hydrogen to the fuel cell stack.

Before the fuel cell stack is assembled, only when the airtightness of each component or related components is secured, efficiency may increase when the fuel cell stack operates. In particular, when the airtightness of a fuel cell system is secured, the efficiency of the fuel cell system may be improved.

An airtightness inspecting method for the fuel cell system according to the related art is a method of determining whether the entire fuel cell stack or the entire FPS leaks. However, according to the method according to the related art, it is difficult to determine in which part of the fuel cell stack or the FPS the leakage occurs or in which component the leakage occurs.

Thus, there is a need for a technology that may identify the leakage for each component unit or each part of the fuel cell stack or the FPS.

SUMMARY

In one aspect, the present disclosure has been made to solve the above-mentioned problems occurring in the existing technologies while advantages achieved by the existing technologies are maintained intact.

An exemplary embodiment of the present disclosure provides a leakage inspecting system for an inspection target that may identify in which component of the inspection target leakage occurs or in which position the leakage occurs as well as whether the leakage occurs in the entire inspection target.

Another embodiment of the present disclosure provides a leakage inspecting system for an inspection target that may finely and accurately perform airtightness inspection on the inspection target, thereby ensuring quality of the inspection target.

The technical problems to be solved by the present disclosure are not limited to the aforementioned problems, and any other technical problems not mentioned herein will be clearly understood from the following description by those skilled in the art to which the present disclosure pertains.

According to an exemplary embodiment of the present disclosure, a leakage inspecting system for an inspection target includes a supply part that supplies a leak inspection gas to the inspection target, a suction part that includes a plurality of inspection pipes facing a plurality of inspection points on the inspection target and suctions the leak inspection gas leaked from the plurality of inspection points through the inspection pipes facing the inspection points, a sensing part that is connected to the suction part and measures a suction amount of the leak inspection gas suctioned through the suction part, and a discharge part that discharges a remaining gas in the inspection target or the suction part to outside thereof.

The leakage inspecting system may further include at least one processor connected to the supply part, the suction part, the sensing part, and the discharge part, and a memory that is connected to the at least one processor and stores instructions, wherein the processor, by executing the instructions, may be configured to control the suction part to suction the leak inspection gas according to each inspection point, control the sensing part to measure the suction amount by the suction part according to each inspection point, and control the discharge part to discharge the leak inspection gas inside the inspection target after the measurement by the sensing part for each inspection point is completed.

The suction part may include a pipe portion including the plurality of inspection pipes, a valve portion including a plurality of inspection valves that are connected to the plurality of inspection pipes and open or close the corresponding inspection pipes, and a suction pipe that connects the valve portion and the sensing part and is provided with a gas moving passage that is a moving passage of a gas flowing from the inspection pipes to the sensing part.

The suction part may further include an orifice installed on the gas moving passage inside the suction pipe.

The processor, by executing the instructions, may be configured to control the valve portion to sequentially open or close the plurality of inspection valves and sense the suction amount of the leak inspection gas measured by the sensing part when the inspection valves are individually opened and determine whether leakage occurs in the inspection points corresponding to the open inspection valves.

The discharge part may include a first discharge portion that is connected to the suction part and discharges the gas remaining in the suction part, and a second discharge portion that is connected to the inspection target and discharges the gas remaining in the inspection target, and wherein the processor, by executing the instructions, may be configured to control the first discharge portion and the second discharge portion to operate before the leak inspection gas is supplied to the inspection target by the supply part.

The first discharge portion may include a first discharge pipe connected to a suction pipe provided in the suction part, a first vacuum pump that is installed on the first discharge pipe and forms a negative pressure smaller than atmospheric pressure inside the first discharge pipe, and a first vacuum opening/closing valve installed on the first discharge pipe and disposed between the suction part and the first vacuum pump.

The second discharge portion may include a second discharge pipe connected to the inspection target, a second vacuum pump that is installed on the second discharge pipe and forms a negative pressure smaller than atmospheric pressure inside the second discharge pipe, and a second vacuum opening/closing valve installed on the second discharge pipe and disposed between the housing and the second vacuum pump.

The discharge part may further include a third discharge portion that is connected to the inspection target and discharges the leak inspection gas inside the inspection target, and wherein the processor, by executing the instructions, may be configured to control the third discharge portion to operate when the measurement by the sensing part is completed.

The discharge part may include a first discharge portion, and wherein the first discharge portion may include a first discharge pipe connected to the suction pipe provided in the suction part, a first vacuum pump that is installed on the first discharge pipe and forms a negative pressure smaller than atmospheric pressure inside the first discharge pipe, and a first vacuum opening/closing valve installed on the first discharge pipe and disposed between the suction part and the first vacuum pump, and the processor may, by executing the instructions, be configured to operate the first vacuum pump and the first vacuum opening/closing valve such that the leak inspection gas flowing from the inspection pipe into the suction pipe is transferred to the sensing part when the inspection valve is opened.

The processor, by executing the instructions, may be configured to perform a reference setting process of setting a reference value based on a value measured by the sensing part before the leak inspection gas is supplied through the supply part, and individually perform the reference setting process before whether the leakage occurs at each of the plurality of inspection points is inspected.

The suction part may further include a helium master that discharges the leak inspection gas in a preset amount, and wherein the processor, by executing the instructions, may be configured to sense a measurement value measured by the sensing part when the helium master operates and determine measurement accuracy of the sensing part.

The suction part may further include a vacuum gauge capable of measuring a pressure of a gas, which is lower than atmospheric pressure.

The pipe portion may further include a master pipe installed to measure a leakage amount leaked throughout the inspection target.

The supply part may further include a relief valve provided to discharge the leak inspection gas outside when a pressure inside the supply pipe is greater than or equal to a predetermined pressure.

The supply part may further include a needle valve for adjusting a flow rate of the gas inside the supply pipe.

The supply part may further include a temperature sensor for measuring a temperature inside the supply pipe.

An end of the inspection pipe may be disposed within about 1 mm from the corresponding inspection point.

The leak inspection gas supplied by the supply part is a helium gas.

The number of inspection pipes is provided to correspond to the inspection points.

As discussed, the method and system suitably include use of a controller or processer.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Hereinafter, embodiments of the present disclosure will be described in detail with reference to the accompanying drawings.

First, the embodiments described below are embodiments suitable for understanding technical features of a leakage inspecting system for an inspection target according to the present disclosure. However, the present disclosure is not limited to the embodiments described below, the technical features of the present disclosure are not limited by the described embodiments, and various modifications may be made within the technical scope of the present disclosure.

Figure 1:
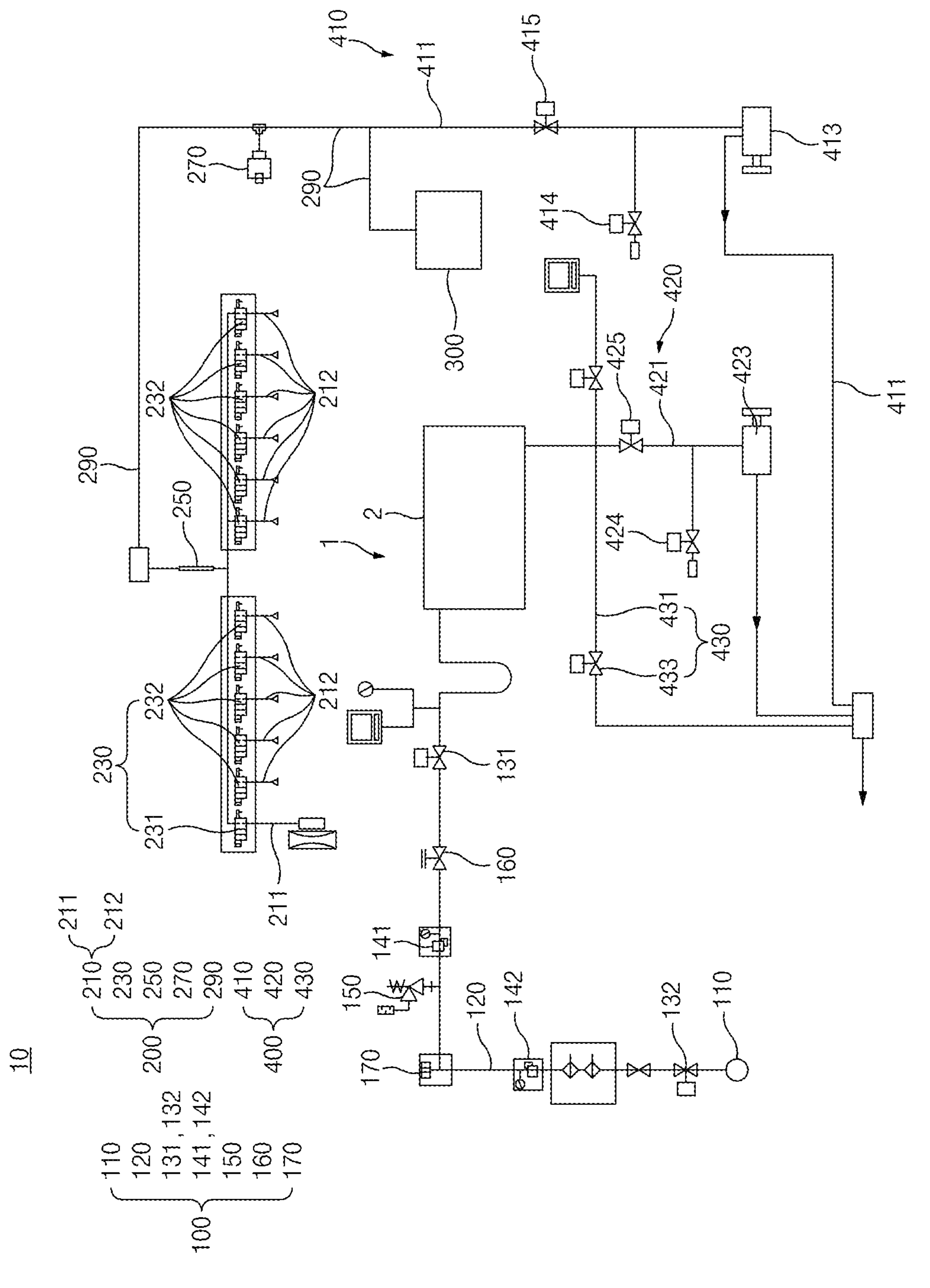
FIG. 1 is a diagram illustrating a leakage inspecting system for an inspection target according to an exemplary embodiment of the present disclosure.
Figure 2:
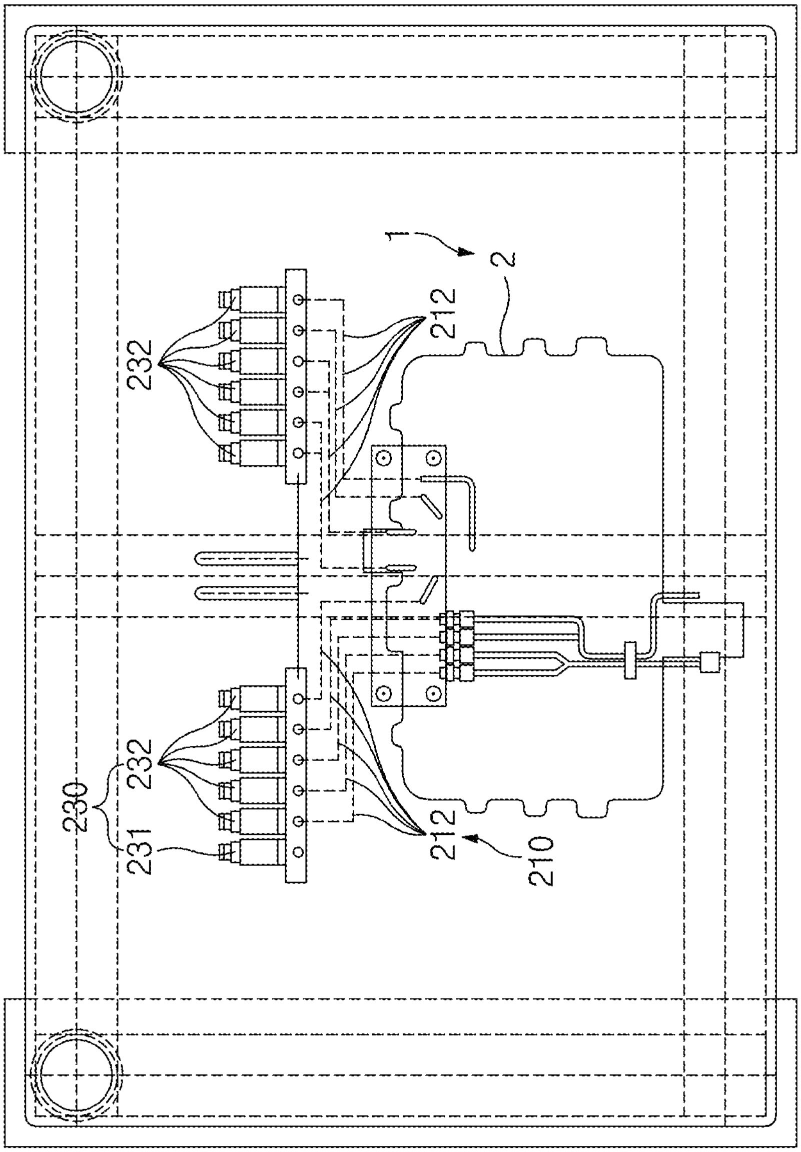
FIG. 2 is a view illustrating an example in which a valve portion and a pipe portion are connected to a fuel processing system (FPS) according to the embodiment of the present disclosure.
Figure 3:
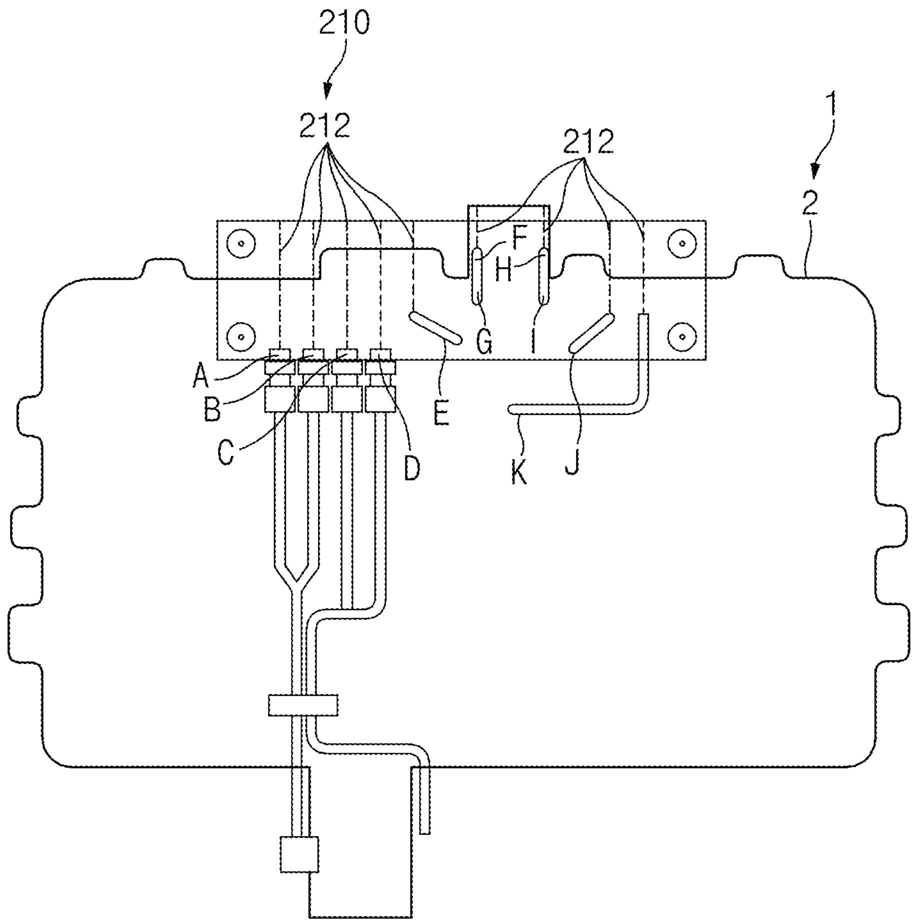
FIG. 3 is an enlarged view of a portion of FIG. 2 and is a view for describing connection between a plurality of inspection points and a plurality of inspection pipes of the FPS.
Figure 4:
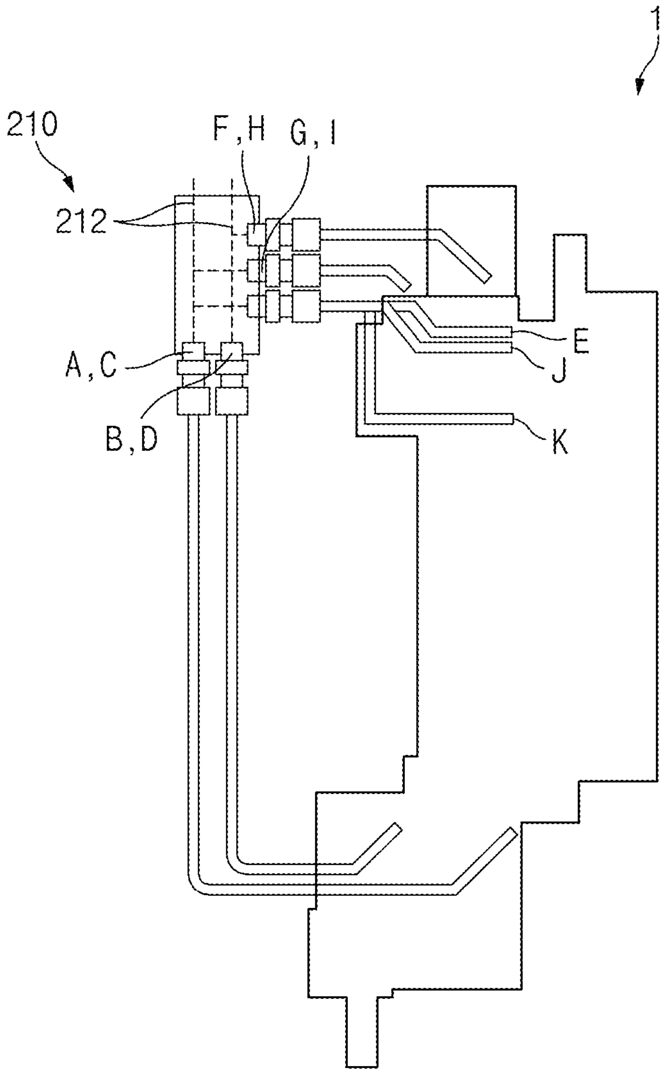
FIG. 4 is a view when viewed from a side surface of FIG. 3.

FIG. 1 is a diagram illustrating a leakage inspecting system for an inspection target according to an exemplary embodiment of the present disclosure, FIG. 2 is a view illustrating an example in which a valve portion and a pipe portion are connected to a fuel processing system (FPS) according to the embodiment of the present disclosure, FIG. 3 is an enlarged view of a portion of FIG. 2 and is a view for describing connection between a plurality of inspection points and a plurality of inspection pipes of the FPS, and FIG. 4 is a view when viewed from a side surface of FIG. 3.

Referring to FIGS. 1 to 4, a leakage inspecting system 10 for an inspection target according to the embodiment of the present disclosure may include a supply part 100, a suction part 200, a sensing part 300, and a discharge part 400.

The supply part 100 may be provided to supply a leak inspection gas to an inspection target 1.

In detail, the supply part 100 is configured to supply the leak inspection gas to the inspection target 1 at a constant pressure and may include various components and various pipes. For example, the inspection target may be the FPS responsible for adjusting the pressure of hydrogen supplied from a hydrogen tank that is a fuel tank to supply the hydrogen to the fuel cell stack. Further, for example, the plurality of inspection points may correspond to a plurality of fastening parts that connect various pipes and various components inside the FPS. FIGS. 3 and 4 illustrate an example of the plurality of inspection points. Parts “A,” “B,” “C,” “D,” “E,” “F,” “G,” “H,” “‘I,” “J,” and “K” in the drawing indicate positions of the inspection points. However, the positions of the inspection points are not limited to the illustrated embodiment and may change depending on a configuration of the inspection target.

Further, the leak inspection gas supplied by the supply part 100 may be, for example, a helium (He) gas.

Hereinafter, a case in which the inspection target 1 is the FPS will be described as an example. However, the inspection target 1 is not limited to the FPS and may be various components, such as fuel cells and batteries, that require detailed airtightness quality assurance.

The suction part 200 may include a plurality of inspection pipes 212 facing the plurality of inspection points on the inspection target 1 and is provided to suction the leak inspection gas leaked from the plurality of inspection points through the inspection pipes 212 facing the inspection points.

In detail, the suction part 200 may be configured to suction the leak inspection gas leaked at each inspection point. The inspection pipes 212 may be installed to face the plurality of inspection points provided in the inspection target 1 and may be provided to suction the leak inspection gas. For example, an end of the inspection pipe 212 may be disposed very close to (e.g., within about 1 mm from) the inspection point. Accordingly, the leak inspection gas leaked from the inspection point may be suctioned.

When the leak inspection gas is supplied to the inspection target 1 by the supply part 100 at a predetermined pressure, leakage may occur at the inspection point at which a degree of the airtightness is insufficient due to a pressure difference between the inspection target 1 and the outside. The suction part 200 may suction the leak inspection gas that has leaked through the inspection pipes 212, may transmit the leak inspection gas to the sensing part 300, and may sense the leak inspection gas.

Here, the suction part 200 may be provided to sequentially suction the leak inspection gas according to each inspection point. Accordingly, the presence or absence and the amount of the leakage at each inspection point may be measured.

The sensing part 300 is connected to the suction part 200 and is provided to measure a suction amount of the leak inspection gas suctioned through the suction part 200.

In detail, the sensing part 300 may serve to receive the leak inspection gas leaked at each inspection pint and suctioned by the suction part 200 and to measure the amount of the leak inspection gas. According to the embodiment of the present disclosure, the sensing part 300 may measure the leakage amount of the leak inspection gas corresponding to each inspection point and may determine whether the leakage occurs at each inspection point based on the measured leakage amount.

For example, the leak inspection gas may be helium, and the sensing part 300 may be a helium detector capable of measuring the amount of helium. However, the type of the sensing part 300 is not limited thereto.

The discharge part 400 may be provided to discharge a gas remaining in the inspection target 1 or the suction part 200 to the outside.

In detail, for accuracy of leakage inspection, the discharge part 400 may serve to discharge the gas and the leak inspection gas remaining in the inspection target 1 and the suction part 200 to the outside before and after the suction amount at the inspection point is measured. In this case, only when the gas remaining in the suction part 200 after each inspection point is inspected as well as the inspection target 1 is discharged as much as possible, accuracy and reliability of the inspection may increase.

In this way, according to the embodiment of the present disclosure, the leakage amount may be measured at each inspection point, and thus in which component of the inspection target 1 the leakage occurs or in which position the leakage occurs as well as whether the leakage occurs in the entire inspection target 1 may be identified.

Further, according to the embodiment of the present disclosure, before and after determining whether the leakage occurs at each inspection point, the gas (including helium) of the inspection target 1 and the suction part 200 is discharged to the outside, and thus reliability of leakage measurement may increase.

Thus, when the embodiment of the present disclosure is used, airtightness inspection may be finely and accurately performed on the inspection target (e.g., the FPS), and thus quality of the inspection target 1 may be ensured.

As an example, when the inspection target 1 is the FPS, it is identified whether the fastening parts are correctly fastened or whether foreign substances are inserted into a coupling part using the leakage inspecting system 10 when an FPS product is manufactured. Thus, quality and reliability of the product may be improved.

Meanwhile, the leakage inspecting system 10 according to the embodiment of the present disclosure may further include at least one processor connected to the supply part 100, the suction part 200, the sensing part 300, and the discharge part 400 and a memory that is connected to the at least one processor and stores instructions.

The processor may include one or more of a central processing unit (CPU), an application processor (AP), or a communication processor (CP). The processor may perform, for example, computations or data processing related to control and/or communication of at least one other component of a hot water supply device. For example, the processor may sense a temperature, a flow rate, and a pressure of the inspection target 1 through various sensors provided in the leakage inspecting system 10 and may control various valves and regulators based on the sensed temperature, the sensed flow rate, and the sensed pressure.

The memory is connected to the at least one processor and stores the instructions. Here, the memory may include a volatile and/or non-volatile memory. Further, the memory may store commands or data related to at least one component of a hot water system 1.

Further, the memory may store instructions for controlling the processor. Hereinafter, an operation performed by the processor may be performed through execution of the instructions stored in the memory.

Further, by executing the instructions, the processor may control the suction part 200 to suction the leak inspection gas at each inspection point and control the sensing part 300 to measure the suction amount at each inspection point using the suction part 200.

Further, by executing the instructions, the processor may control the discharge part 400 so that the leak inspection gas inside the inspection target 1 is discharged after the measurement by the sensing part 300 at each inspection point is completed.

In detail, the processor may control an operation of the leakage inspecting system 10 for the inspection target 1 and may determine whether the leakage occurs at each inspection point based on the measurement amount measured by the sensing part 300. In this case, the processor may control to perform the leakage inspection at each inspection point.

In more detail, when whether the leakage occurs in one inspection point among the plurality of inspection points is inspected, the processor may first operate the discharge part 400 to discharge all the gases in the inspection target 1 and the suction part 200 to the outside. Thereafter, the supply part 100 may be operated to supply and press the leak inspection gas to the inspection target 1 at a constant pressure.

The processor may operate the suction part 200 to suction the leak inspection gas leaked to the inspection pipe 212 disposed adjacent to each inspection point, may allow the sensing part 300 to measure the suctioned leak inspection gas, and thus may measure the leakage amount at each inspection point. Further, the processor may determine whether the leakage occurs at each inspection point based on the measurement amount of the sensing part 300.

When whether the leakage occurs at one inspection point is completely determined, the processor may operate the discharge part 400 to discharge the leak inspection gas remaining in the inspection target 1 to the outside. Accordingly, influence of any one inspection point on inspection of another inspection point may be minimized due to the leaked leak inspection gas leaked or the gas remaining in the leakage inspecting system 10. In particular, when a helium gas is used as the leak inspection gas, helium is light but does not spread quickly into the air in nature, which may affect diagnosis of other inspection points. Thus, when whether the leakage occurs at any one inspection point is completely diagnosed, a process of discharging the helium gas to the outside through the discharge part 400 is required.

Further, the processor may repeatedly perform the above-described process when whether the leakage occurs at another inspection point is inspected.

Meanwhile, the inspection target 1 may include a housing 2 in which the plurality of inspection points are arranged. Further, the supply part 100 may be provided to supply the leak inspection gas to the entire inspection target 1 or each inspection point.

In detail, the supply part 100 may include a supply source 110 provided to supply the leak inspection gas and a supply pipe 120 that connects the supply source 110 to the inspection target 1 or each inspection point.

Further, the supply part 100 may include supply valves 131 and 132 that are installed on the supply pipe 120 and open or close the supply pipe 120 and pressure regulators 141 and 142 that are installed on the supply pipe 120 and adjust a supply amount of the leak inspection gas supplied to the housing 2. Here, the supply valves 131 and 132 and the pressure regulators 141 and 142 may be provided in one or more.

Through this configuration, the supply part 100 may supply the leak inspection gas to the inspection target 1 at a preset pressure. Here, the supply part 100, for example, the supply valves 131 and 132 and the pressure regulators 141 and 142, may be electrically connected to the processor. Further, the processor may control operations of the supply valves 131 and 132 and the pressure regulators 141 and 142 to determine if leakage occurs at each inspection point.

For example, the supply part 100 may further include a relief valve 150 provided to discharge the leak inspection gas to the outside when a pressure inside the supply pipe 120 is greater than or equal to a predetermined pressure, a needle valve 160 for adjusting a flow rate of the gas inside the supply pipe 120, and a temperature sensor 170 for measuring a temperature inside the supply pipe 120.

Meanwhile, the suction part 200 according to the embodiment of the present disclosure may include a pipe portion 210, a valve portion 230, and a suction pipe 290.

The pipe portion 210 may include a plurality of inspection pipes 212.

Further, the valve portion 230 may include a plurality of inspection valves 232 connected to the plurality of inspection pipes 212 and provided to open or close the corresponding inspection pipes 212.

For example, the number of inspection pipes 212 may be provided to correspond to the inspection points. One end of the inspection pipe 212 may be disposed adjacent to the inspection point to face the inspection point, and the other end of the inspection pipe 212 may be connected to the inspection valve 232.

Here, the pipe portion 210 may further include a master pipe 211 installed to measure the leakage amount leaked throughout the inspection target 1. Further, the valve portion 230 may include a master valve 231 connected to the master pipe 211. Therefore, whether the leakage occurs at the entire inspection target 1 may be diagnosed.

The suction pipe 290 may be provided with a gas moving passage as a moving passage that connects the valve portion 230 and the sensing part 300 and is provided for a gas flowing from the inspection pipe 212 to the sensing part 300.

In detail, one end of the suction pipe 290 may have a gas moving passage that connects the valve portion 230 and the sensing part 300, facilitating the flow of gas from the inspection pipe 212 to the sensing part 300.

Further, the suction part 200 may further include an orifice 250 installed on the gas moving passage inside the suction pipe 290. In the embodiment of the present disclosure, the suction part 200 includes the orifice 250, and thus the leak inspection gas may be finely measured.

For example, the suction part 200 may further include a vacuum gauge 270 capable of measuring a pressure of a gas, which is lower than atmospheric pressure.

Here, the processor may control the valve portion 230 to sequentially open or close the plurality of inspection valves 232.

Further, the processor may sense the amount of suction of the leak inspection gas measured by the sensing part 300 when each inspection valve 232 is individually opened, and thus may determine whether the leakage occurs at the inspection point corresponding to the open inspection valve 232.

In detail, the processor may control the inspection valves 232 to open or close individually and may allow the sensing part 300 to measure the amount of helium leaked at each inspection point. Accordingly, when the embodiment of the present disclosure is used, the accurate amount of leakage may be sensed as well as whether the leakage occurs at each inspection point is sensed simply.

The valve portion 230 and the sensing part 300 are controlled by the processor, and thus the leakage inspecting system 10 may be automatically operated.

Meanwhile, a detailed configuration of the discharge part 400 will be described below with reference to FIG. 1.

The discharge part 400 may include a first discharge portion 410, a second discharge portion 420, and a third discharge portion 430.

The first discharge portion 410 may be connected to the suction part 200 and may be provided to discharge the gas remaining in the suction part 200.

In detail, the first discharge portion 410 may include a first discharge pipe 411, a first vacuum pump 413, and a first vacuum opening/closing valve 415.

The first discharge pipe 411 may be connected to the suction pipe 290 provided in the suction part 200. Further, the first vacuum pump 413 may be installed on the first discharge pipe 411 and may be provided to form a negative pressure lower than atmospheric pressure inside the first discharge pipe 411.

Further, the first vacuum opening/closing valve 415 may be installed on the first discharge pipe 411 and disposed between the suction part 200 and the first vacuum pump 413.

In detail, when the negative pressure is formed in the first discharge pipe 411 by the first vacuum pump 413, the remaining gas in the suction pipe 290 and the inspection valve 232 may be suctioned due to this pressure, and then discharged outside. Meanwhile, the first discharge portion 410 may further include a first vacuum pump exhaust valve 414 provided to discharge the gas to form the negative pressure in the first discharge pipe 411.

Further, the processor may control the first discharge portion 410 to operate before the leak inspection gas is supplied to the inspection target 1 by the supply part 100.

In detail, before the leakage amount at each inspection point is measured, the first discharge portion 410 may be operated to discharge all the gas in the suction part 200. Accordingly, inspection accuracy of a next inspection point may be improved.

The second discharge portion 420 may be connected to the inspection target 1 and may be provided to discharge the gas remaining in the inspection target 1.

In detail, the second discharge portion 420 may include a second discharge pipe 421, a second vacuum pump 423, and a second vacuum opening/closing valve 425.

The second discharge pipe 421 may be connected to the inspection target 1. Further, the second vacuum pump 423 may be installed on the second discharge pipe 421 and may be provided to form a negative pressure lower than atmospheric pressure within the second discharge pipe 421.

Further, the second vacuum opening/closing valve 425 may be installed on the second discharge pipe 421 and disposed between the housing 2 and the second vacuum pump 423.

In detail, when the negative pressure is formed in the second discharge pipe 421 by the second vacuum pump 423, the gas remaining in the inspection target 1 may be suctioned due to the pressure, and the suctioned gas may be discharged to the outside. Meanwhile, the second discharge portion 420 may further include a second vacuum pump exhaust valve 424 provided to discharge the gas to form the negative pressure in the second discharge pipe 421.

Further, the processor may control the second discharge portion 420 to operate before the leak inspection gas is supplied to the inspection target 1 by the supply part 100.

In detail, before the leakage amount of each inspection point is measured, the second discharge portion 420 may be operated to discharge the gas in the inspection target 1 and the inspection point as much as possible. Accordingly, inspection accuracy of a next inspection point may be improved.

Meanwhile, the first discharge portion 410 may also serve to move, to the sensing part 300, the leak inspection gas flowing through the gas moving passage of the suction pipe 290.

In detail, the processor may control operations of the first vacuum pump 413 and the first vacuum opening/closing valve 415 so that the leak inspection gas flowing from the inspection pipe 212 to the suction pipe 290 is transmitted to the sensing part 300 when the inspection valve 232 is opened.

Accordingly, the leak inspection gas leaked at each inspection point may move to the sensing part 300 due to its own pressure. However, the negative pressure is formed in the suction pipe 290 connected to the first discharge pipe 411 by the first vacuum pump 413, and thus the leak inspection gas may move to the sensing part 300 by a suctioning force. Accordingly, the movement of the leak inspection gas to the sensing part 300 becomes smooth, and thus reliability of the measurement of the suction amount by the sensing part 300 may increase.

The third discharge portion 430 may be connected to the inspection target 1 and may be provided to discharge the leak inspection gas inside the inspection target 1.

Further, when the measurement by the sensing part 300 is completed, the processor may control the third discharge portion 430 to operate.

In detail, the third discharge portion 430 may include an exhaust pipe 431 connected to the inspection target 1 and an exhaust valve 433 that opens or closes the exhaust pipe 431. Further, the processor may control the exhaust valve 433 to be opened when the leakage amount at any one inspection point is completely measured. Accordingly, the leak inspection gas supplied to the inspection target 1 may be discharged to the outside, and accuracy of leakage inspection for an inspection point to be inspected next may increase.

In this way, in the embodiment of the present disclosure, the first discharge portion 410, the second discharge portion 420, and the third discharge portion 430 are connected to the processor, operations thereof are controlled by the processor, and thus, air blowing may be automatically performed before and after the leakage amount at the inspection point is measured.

However, in the embodiment of the present disclosure, the discharge of the gas remaining in the inspection target 1 or the suction part 200 is not limited to automatic performing and may be also performed manually by an operator. For example, in the embodiment of the present disclosure, an air gun may be additionally provided. Further, when the processor determines that the leakage occurs at the inspection point, the helium of the inspection target 1 may be discharged by the third discharge portion 430 as well as the operator may manually discharge the helium using the air gun.

Meanwhile, in the embodiment of the present disclosure, a process for further improving the reliability of leakage inspection may be additionally performed.

As an example, a reference setting process of setting a reference value based on a value measured by the sensing part 300 may be performed before the leak inspection gas is supplied through the supply part 100. Further, the processor may individually perform the reference setting process before the leakage inspection at each of the plurality of inspection points.

In detail, a measurement value of the suction amount may vary depending on lengths of the inspection pipe 212 and the suction pipe 290 provided between the inspection target 1 or the inspection point and the sensing part 300, and thus a process for increasing the accuracy is required.

The reference setting process may be a process of setting the reference value of the inspecting system before the leak inspection gas is supplied by the supply part 100. Before the leak inspection gas is supplied to the inspection target 1 and the inspecting system by the supply part 100, the sensing part 300 may measure the amount of the leak inspection gas present in the system and may set the measured amount as the reference value.

In this case, the reference setting process may be performed whenever the leakage is diagnosed at each inspection point. That is, the reference setting process may always be performed before each inspection. This is to respond to a case in which an initial value changes due to the gas remaining in the inspection for a previous inspection point.

As another example, the suction part 200 may further include a helium master provided to discharge a preset amount of the leak inspection gas. Further, when the helium master operates, the processor may sense a measurement value measured by the sensing part 300 and determine measurement accuracy of the sensing part 300.

A reliability measurement process of the processor according to another example may be a process of identifying the accuracy of the sensing part 300 and adjusting sensitivity thereof. In detail, since the helium master is a member that discharge a set amount of leak inspection gas, the processor may measure the amount of leak inspection gas reduced by the sensing part 300 after the helium master is operated and thus may determine the accuracy of the sensing part 300. In this case, when there is a difference between the amount discharged by the operation of the helium master and the amount of reduction measured by the sensing part 300, accuracy of the inspection may increase by adjusting the sensitivity of the sensing part 300. Accordingly, the reliability of leakage inspection for the inspection target 1 according to the embodiment of the present disclosure may be improved.

Meanwhile, an operation of the leakage inspecting system 10 of the inspection target 1 according to the embodiment of the present disclosure will be described below with reference to FIGS. 1 to 4.

When whether the leakage occurs at any one inspection point among the plurality of inspection points is inspected, first, the first vacuum pump 413 of the second discharge portion 420 may be operated to discharge the gas in the inspection target 1 to the outside as much as possible. For example, a vacuum state may be formed in the inspection target 1 through the first vacuum pump 413. However, the present disclosure is not limited thereto, and the first vacuum pump 413 may be operated to form the negative pressure so as to discharge the gas in the inspection target 1 as much as possible.

Further, the second vacuum pump 423 of the second discharge portion 420 is operated to discharge the gas in the inspection pipe 212 and the suction pipe 290 to the outside as much as possible. For example, the second vacuum pump 423 may be operated to form a vacuum state in the inspection pipe 212 and the suction pipe 290 connected to the sensing part 300. However, the present disclosure is not limited thereto, and the second vacuum pump 423 may be operated to form the negative pressure so as to discharge the gas in the inspection target 1 as much as possible.

In this way, before whether the leakage occurs at each inspection point is diagnosed, the negative pressure may be formed in the inspection target and the pipes connected to the sensing part 300, and thus the accuracy of the inspection may increase.

Thereafter, the supply valves 131 and 132 and the pressure regulators 141 and 142 may be operated to supply the leak inspection gas to the inspection target 1 at a constant pressure (e.g., about 1.5 bar). In this case, a pressure may be applied to the inspection point of the inspection target 1 due to the pressure of the supplied gas, and when the airtightness is insufficient, the leakage occurs, and thus the leak inspection gas may be suctioned to the inspection pipe 212.

In this case, the leak inspection gas suctioned by the suction part 200 may move to the sensing part 300 by its own pressure and the operation of the first discharge portion 410. The sensing part 300 may measure the leakage amount of the leak inspection gas. Further, the processor may determine whether the leakage occurs at the inspection point and the amount of leakage, based on the measurement amount of the sensing part 300.

When whether the leakage occurs at any one inspection point is completely determined, the third discharge portion 430 may be operated to discharge the leak inspection gas remaining in the inspection target 1 to the outside. Accordingly, influence of any one inspection point on inspection of another inspection point may be minimized due to the leaked leak inspection gas leaked or the gas remaining in the leakage inspecting system 10. For example, when whether the leakage occurs at each inspection point is completely determined and inspected, the exhaust pipes are connected to a front end and a rear end of the inspection target 1, the exhaust valves are opened, air blows at a predetermined pressure (e.g., about 2 bar) for a predetermined time (e.g., about 20 seconds), and then a next inspection point may be inspected. However, the method of discharging the remaining gas by the third discharge portion (e.g., a time, a pressure or the like) is not limited to the above description.

In particular, when the helium gas is used as the leak inspection gas, the helium is light but does not spread quickly into the air in nature, which may affect diagnosis of other inspection points. Thus, when whether the leakage occurs at any one inspection point is completely diagnosed, the helium gas is discharged to the outside through the third discharge portion 430, and thus influence on inspection at other inspection points may be minimized.

Further, the processor may perform the above process for any one inspection point and then may repeat the above process when whether the leakage occurs at another inspection point is inspected.

In this way, according to the embodiment of the present disclosure, the leakage amount may be measured at each inspection point. Thus, in which component of the inspection target the leakage occurs or in which position the leakage occurs as well as whether the leakage occurs in the entire inspection target may be identified.

Further, according to the embodiment of the present disclosure, before and after the leakage occurring in each inspection point is diagnosed, the gas in the inspection target and the suction part is discharged to the outside, and thus the reliability of measurement of the leakage amount may increase.

Thus, when the embodiment of the present disclosure is used, airtightness inspection for the inspection target may be performed finely and accurately, and thus quality of the inspection target may be ensured.

Although specific embodiments of the present disclosure have been described above, the spirit and scope of the present disclosure are not limited thereto, and those skilled in the art to which the present disclosure pertains may derive various modifications and changes without changing the subject matter of the present disclosure described in the appended claims.

What is claimed is:

1. A leakage inspecting system for an inspection target, the leakage inspecting system comprising:

a supply part configured to supply a leak inspection gas to the inspection target;

a suction part comprising a plurality of inspection pipes facing a plurality of inspection points on the inspection target and configured to suction the leak inspection gas leaked from the plurality of inspection points through the inspection pipes facing the inspection points;

a sensing part connected to the suction part and configured to measure a suction amount of the leak inspection gas suctioned through the suction part; and a discharge part configured to discharge a remaining gas in the inspection target or the suction part outside thereof.

2. The leakage inspecting system of claim 1, further comprising:

at least one processor connected to the supply part, the suction part, the sensing part, and the discharge part; and a memory connected to the at least one processor and configured to store instructions, wherein the processor is configured to, by executing the instructions:

control the suction part to suction the leak inspection gas according to each inspection point;

control the sensing part to measure the suction amount by the suction part according to each inspection point; and control the discharge part to discharge the leak inspection gas inside the inspection target after the measurement by the sensing part for each inspection point is completed.

3. The leakage inspecting system of claim 2, wherein the suction part comprises:

a pipe portion comprising the plurality of inspection pipes;

a valve portion comprising a plurality of inspection valves connected to the plurality of inspection pipes and configured to open or close the corresponding inspection pipes; and a suction pipe configured to connect the valve portion and the sensing part and provided with a gas moving passage that is a moving passage of a gas flowing from the inspection pipes to the sensing part.

4. The leakage inspecting system of claim 3, wherein the suction part further comprises:

an orifice installed on the gas moving passage inside the suction pipe.

5. The leakage inspecting system of claim 3, wherein the processor is configured to, by executing the instructions:

control the valve portion to sequentially open or close the plurality of inspection valves; and sense the suction amount of the leak inspection gas measured by the sensing part when the inspection valves are individually opened and determine whether leakage occurs in the inspection points corresponding to the open inspection valves.

6. The leakage inspecting system of claim 3, wherein the discharge part comprises a first discharge portion, and wherein the first discharge portion comprises:

a first discharge pipe connected to the suction pipe provided in the suction part;

a first vacuum pump installed on the first discharge pipe and configured to form a negative pressure smaller than atmospheric pressure inside the first discharge pipe; and a first vacuum opening/closing valve installed on the first discharge pipe and disposed between the suction part and the first vacuum pump, and wherein the processor is configured to, by executing the instructions, operate the first vacuum pump and the first vacuum opening/closing valve such that the leak inspection gas flowing from the inspection pipe into the suction pipe is transferred to the sensing part when the inspection valve is opened.

7. The leakage inspecting system of claim 3, wherein the suction part further comprises a vacuum gauge capable of measuring a pressure of a gas, which is lower than atmospheric pressure.

8. The leakage inspecting system of claim 3, wherein the pipe portion further comprises a master pipe installed to measure a leakage amount leaked throughout the inspection target.

9. The leakage inspecting system of claim 2, wherein the discharge part comprises:

a first discharge portion connected to the suction part and configured to discharge the remaining gas in the suction part; and a second discharge portion connected to the inspection target and configured to discharge the remaining gas in the inspection target, and wherein the processor is configured to, by executing the instructions, control the first discharge portion and the second discharge portion to operate before the leak inspection gas is supplied to the inspection target by the supply part.

10. The leakage inspecting system of claim 9, wherein the first discharge portion comprises:

a first discharge pipe connected to a suction pipe provided in the suction part;

a first vacuum pump installed on the first discharge pipe and configured to form a negative pressure smaller than atmospheric pressure inside the first discharge pipe; and a first vacuum opening/closing valve installed on the first discharge pipe and disposed between the suction part and the first vacuum pump.

11. The leakage inspecting system of claim 9, wherein the second discharge portion comprises:

a second discharge pipe connected to the inspection target;

a second vacuum pump installed on the second discharge pipe and configured to form a negative pressure smaller than atmospheric pressure inside the second discharge pipe; and a second vacuum opening/closing valve installed on the second discharge pipe and disposed between the inspection target and the second vacuum pump.

12. The leakage inspecting system of claim 2, wherein the discharge part further comprises:

a third discharge portion connected to the inspection target and configured to discharge the leak inspection gas inside the inspection target, and wherein the processor is configured to, by executing the instructions, control the third discharge portion to operate when the measurement by the sensing part is completed.

13. The leakage inspecting system of claim 2, wherein the processor is configured to, by executing the instructions:

perform a reference setting process of setting a reference value based on a value measured by the sensing part before the leak inspection gas is supplied through the supply part; and individually perform the reference setting process before whether the leakage occurs at each of the plurality of inspection points is inspected.

14. The leakage inspecting system of claim 2, wherein the suction part further comprises:

a helium master configured to discharge the leak inspection gas in a preset amount, and wherein the processor is configured to, by executing the instructions, sense a measurement value measured by the sensing part when the helium master operates, and determines measurement accuracy of the sensing part.

15. The leakage inspecting system of claim 1, wherein the supply part further includes a relief valve provided to discharge the leak inspection gas outside when a pressure inside the supply pipe is greater than or equal to a predetermined pressure.

16. The leakage inspecting system of claim 1, wherein the supply part further includes a needle valve for adjusting a flow rate of the gas inside the supply pipe.

17. The leakage inspecting system of claim 1, wherein the supply part further includes a temperature sensor for measuring a temperature inside the supply pipe.

18. The leakage inspecting system of claim 1, wherein an end of the inspection pipe is disposed within about 1 mm from the corresponding inspection point.

19. The leakage inspecting system of claim 1, wherein the leak inspection gas supplied by the supply part is a helium gas.

20. The leakage inspecting system of claim 1, wherein the number of inspection pipes is provided to correspond to the inspection points.

* * * * *